United States Patent
Goebel et al.

(10) Patent No.: US 10,040,822 B2
(45) Date of Patent: Aug. 7, 2018

(54) NEUROPROTECTIVE COMPOSITION AND METHOD OF USE

(71) Applicants: Brown University, Providence, RI (US); Wayne State University, Detroit, MI (US)

(72) Inventors: Dennis J. Goebel, Wixom, MI (US); John Marshall, Barrington, RI (US)

(73) Assignee: National Institutes of Health, U.S. Dept. of Health and Human Services, NIH Division of Extramural Inventions and Technology Resources, Bethesda, MD (US)

( * ) Notice: Subject to any disclaimer, the term of this patent is extended or adjusted under 35 U.S.C. 154(b) by 0 days.

(21) Appl. No.: 15/393,720

(22) Filed: Dec. 29, 2016

(65) Prior Publication Data

US 2017/0107253 A1   Apr. 20, 2017

Related U.S. Application Data

(63) Continuation of application No. 14/391,293, filed as application No. PCT/US2013/036938 on Apr. 17, 2012, now abandoned.

(51) Int. Cl.
*C07K 7/06* (2006.01)
*A61K 9/00* (2006.01)
*A61K 38/08* (2006.01)
*A61K 38/00* (2006.01)

(52) U.S. Cl.
CPC ............. *C07K 7/06* (2013.01); *A61K 9/0019* (2013.01); *A61K 38/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,229,961 B2 * | 6/2007 | Rothbard | A61K 31/155 514/1.2 |
| 7,820,626 B2 | 10/2010 | Rothbard et al. | |
| 2011/0028394 A1 | 2/2011 | Karim et al. | |
| 2011/0053829 A1 | 3/2011 | Baumhof et al. | |

FOREIGN PATENT DOCUMENTS

| | | |
|---|---|---|
| WO | 2010150708 A1 | 12/2010 |
| WO | 2013158739 A1 | 10/2013 |

OTHER PUBLICATIONS

Meloni et al. (J. Cereb Blood Flow Metab. vol. 35, 2015).*
Hyun et al. ("Therapeutic effects of a reducible poly (oligo-D-arginine) carrier with the heme oxygenase-1 gene in the treatment of hypoxic ischemic brain injury" Biomaterials, vol. 31, Issue 34, Dec. 2010;pp. 9128-9134).*
European Search Report dated Oct. 28, 2015, issued in European Application No. 13777758.7.
Zhang, R., et al., "Dependence of Formation of Small Disulfide Loops in Two-Cysteine Peptides on the Number and Types of Intervening Amino Acids", The Journal of Biological Chemistry, Nov. 1989, vol. 264, No. 31, pp. 18478-18479.
International Application No. PCT/US2013/036938 International Search Report dated Aug. 13, 2013.
Hyun, H., et al., "Therapeutic Effects of a Reductible Poly (oligo-D-arginine) Carrier with the Heme Oxygenase-1 Gene in the Treatment of Hypoxic-Ischemic Brain Injury", Biomaterials 31, 2010, pp. 9128-9134.
Meloni, B., et al., "Poly-Arginine and Arginine-Rich Peptides are Neuroprotective in Stroke Models", Journal of Cerebral Blood Flow & Metabolism, 2015, No. 35, pp. 993-1004.
Subrizi, A., et al., "Tat (48-60) Peptide Amino Acide Sequence is Not Unique in its Cell Penetrating Properties and Cell-Surface Glycosaminoglycans Inhibit its Cellular Uptake", Journal of Controlled Release, 2012, No. 158, pp. 277-285.
Trivedi, M., et al., "The Role of Thiols and Disulfides in Protein Chemical and Physical Stability", Curr Protein Pept. Sci., Dec. 2009, pp. 614-625.
Marshall, J., et al., "Inhibition of N-Methyl-D-Aspartate-Indiced Retinal Neuronal Death by Polyarginine Peptides is Linked to the Attenuation of Stress-Indiced Hyperpolarization of the Inner Mitochondrial Membrane Potential", The Journal of Biological Chemistry, Sep. 2015, vol. 290, No. 36, pp. 22030-22048.
American Heart Association, "Intracoronary KAI-9803 as an Adjunct to Primary Percutaneous Coronary Intervention fo Acute ST-Segment Elevation Myocardial Infarction", Circulation Journal of the American Heart Association, Feb. 2008.
Chen, L., et al., "Molecular Transporters for Peptides: Delivery of a Cardioprotective □PKC Agonist Peptide into cells and Intact Ischemic Heart using a Transport System, R7", Chemistry & Biology, 2001, pp. 1123-1129.
Shahana, S., et al., "Effects of the Cationic Protein Poly-L-Arginine on Airway Epithelial Cells In Vitro", Mediators of Inflammation, 2002, pp. 141-148.
Miyaji, Y., et al., "Distribution of KAI-9803, a Novel □Protein Kinase C Inhibitor, after Intravenous Administration to Rats", Drug Metabolism and Disposition: The Biological Fate of Chemicals, Oct. 2011, vol. 39, Issue 10.

* cited by examiner

*Primary Examiner* — James H Alstrum-Acevedo
*Assistant Examiner* — Tara L Martinez
(74) *Attorney, Agent, or Firm* — Polsinelli, PC

(57) ABSTRACT

A therapeutic composition for treating brain injury comprising a polyarginine peptide of from 5 to 9 arginines (SEQ ID NO: 1), and further comprising 1 or more terminal cysteines. The composition is administered in therapeutically effective dosages prophylactically or as soon as possible post-injury in treating neuronal injury.

6 Claims, No Drawings

```
SEQUENCE LISTING

<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: Residues may be D or L configuration
<220> FEATURE:
<221> NAME/KEY: misc_feature
<222> LOCATION: (1)..(9)
<223> OTHER INFORMATION: This sequence may encompass 5 to 9 residues

<400> SEQUENCE: 1

Arg Arg Arg Arg Arg Arg Arg Arg Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Residues may be D or L configuration

<400> SEQUENCE: 2

Cys Arg Arg Arg Arg Arg Cys
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Residues may be D or L configuration

<400> SEQUENCE: 3

Arg Arg Arg Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Residues may be D or L configuration

<400> SEQUENCE: 4

Arg Arg Arg Arg Arg Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Residues may be D or L configuration

<400> SEQUENCE: 5

Arg Arg Arg Arg Arg Arg Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: Residues may be D or L configuration

<400> SEQUENCE: 6

Arg Arg Arg Arg Arg Arg Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: Residues may be D or L configuration
```

```
<400> SEQUENCE: 7

Arg Arg Arg Arg Arg Arg Arg Arg Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(8)
<223> OTHER INFORMATION: Residues may be D or L configuration

<400> SEQUENCE: 8

Cys Arg Arg Arg Arg Arg Arg Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Residues may be D or L configuration

<400> SEQUENCE: 9

Cys Arg Arg Arg Arg Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Residues may be D or L configuration

<400> SEQUENCE: 10

Cys Arg Arg Arg Arg Arg Arg Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Residues may be D or L configuration

<400> SEQUENCE: 11

Cys Arg Arg Arg Arg Arg Arg Ala Ala
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Residues may be D or L configuration

<400> SEQUENCE: 12

Arg Arg Arg Arg Arg Arg Arg Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Residues are D configuration

<400> SEQUENCE: 13

Cys Arg Arg Arg Arg Arg Arg Arg
1               5
```

NEUROPROTECTIVE COMPOSITION AND METHOD OF USE

CROSS REFERENCE TO RELATED APPLICATIONS

This application is a continuation of U.S. application Ser. No. 14/391,293 filed on Oct. 8, 2014 which is a 371 application of PCT/US2013/036938, filed on Apr. 17, 2013, which claims priority to U.S. provisional application No. 61/625,349, filed on Apr. 17, 2012, which are expressly incorporated by reference in their entirety.

STATEMENT OF GOVERNMENTAL RIGHTS

This invention was made with government support under National Institute for Neurological Disorders of the NIH Grant #:R21-NS031176 and National Eye Institute of the NIH Grant #:R01-EY014430. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 3, 2013, is named B019-7033WO0_SL.txt and is 4,333 bytes in size.

FIELD OF THE INVENTION

The polyarginine and polyarginine/cysteine compositions disclosed here provide therapeutic options for neurological insult with particular reference to stroke, traumatic brain injury, and spinal cord injury (collectively "neuronal injury"). Specific note is made of the compositions of this invention moderating or avoiding the pathologic metabolic cascades associated with stroke, traumatic brain injury (TBI) and retinal damage as a result of glaucoma. Treatment of macular degeneration is also noted.

BACKGROUND OF THE INVENTION

A stroke, or cerebrovascular accident (CVA), is the rapid loss of brain function due to disturbance in the blood supply to the brain. This can be due to ischemia (lack of blood flow) caused by blockage (thrombosis, arterial embolism), or a hemorrhage (broadly termed "neurological insult"). As a result, and often worsening over time, brain injury becomes permanent dysfunction/damage. Typically, affected areas of the brain have diminished or complete loss of function. In particular instances this is exhibited as an inability or reduced ability to move one or more limbs on one side of the body, inability to or difficulty in understanding or formulating speech, or an inability to see one side of the visual field. In the case of stroke, secondary neuronal damage following the initial insult is a significant factor in patient decline and eventual death. This decline manifests itself weeks to months following the initial stoke and, without effective therapeutic intervention, leads to a slow but continuous decline in the patients physical and mental health.

In the case of TBI, the progression of damage is typically slower than that in stroke. Recent reports, however, establish TBI as equally destructive in outcome in the more severe cases Current reports find that about 40% of people with TBI exhibit a continuing decline in both physical and mental capacity. This represents a significantly higher incidence of dementia, in some instances is an aggravating factor in death.

An important consideration in therapeutic treatment and improved outcomes in patients afflicted with neuronal injury (including either Stroke or TBI) is to block secondary injury of surrounding neurons that were not, in the first instance, directly affected by the primary insult. Literature reports that secondary neuronal damage occurs after a variety of brain insults including subarachnoid hemorrhage, stroke, and traumatic brain injury and involves metabolic cascades. Noted metabolic aspects include prolonged secondary ischemia, cerebral hypoxia, hypotension, cerebral edema, changes in the blood flow to the brain; and raised intracranial pressure. Other secondary insults include hypercapnia, acidosis, meningitis, and brain abscess. In addition, alterations in the release of neurotransmitters particularly glutamate can cause excitotoxic neuronal cell death by causing free radicals generation and oxidative stress within these neurons that leads to neurodegeneration.

The following references are noted, the teachings of which are incorporated by reference in their entirety:

1. The Behavioral and Cognitive Neurology of Stroke Ed. Olivier Godefroy (Cambridge University Press, 2nd edition, 2013);
2. Stroke Rehabilitation: A Function-Based Approach, 3rd, Ed. Glen Gilled, (Mosby, 2010);
3. Stroke Part III: Investigation and management, Volume 94: Handbook of Clinical Neurology (Series Editors: Aminoff, Boller and Swaab, Ed. Marc Fisher (Elsiver 2009);
4. Traumatic Brain Injury: Methods for Clinical and Forensic Neuropsychiatric Assessment, Second Edition, Robert P. Granacher Jr. (CRC Press 2007);
5. Sports Neuropsychology: Assessment and Management of Traumatic Brain Injury, Ed. Ruben J. Echemendia PhD (The Guilford Press, 2006);
6. Brain Injury Medicine: Principles and Practice, Second Edition Ed. Nathan D. Zasler MD (Demos Medical; 2012); and
7. Blockade of PARP activity attenuates poly(ADP-ribosyl)ation but offers only partial neuroprotection against NMDA-induced cell death in the rat retina. (Goebel and Winkler, J Neuro Chem, 98:1732-1745, 2006) (NMDA-induced chemical stroke in vivo rat retinal neurotoxicity model).

Reference is made to the Glasgow Coma Scale. The Glasgow Coma Scale 15-point test used to assess the initial severity of a brain injury by checking a person's ability to follow directions and move their eyes and limbs. Abilities are scored numerically. Higher scores mean milder injuries.

SUMMARY OF THE INVENTION

The compositions of this invention include a polyarginine peptide of from 5 to 9 arginines (SEQ ID NO: 1). Both d- and l-arginine is contemplated. The compositions may further include 1 terminal cysteine. Terminal cysteines may be either N-terminus or C-terminus cysteines. Options also include the addition of a second cysteine that is linked to the terminal cysteine on the peptide by a disulfide bridge, and/or the placement of a terminal cysteine on both ends of the R(5+n) peptide (SEQ ID NO: 2), with or without the addition of two additional cysteines via disulfide linkage. Particular reference is made to the following compositions. A polyarginine with between 5 and 9 arginines (SEQ ID NO: 1): RRRRR also termed R(5) (SEQ ID NO: 3). Similarly, R(6) (SEQ ID NO: 4), R(7) (SEQ ID NO: 5), R(8) (SEQ ID NO: 6) and R(9) (SEQ ID NO: 7). Both l- and d-amino acids are contemplated.

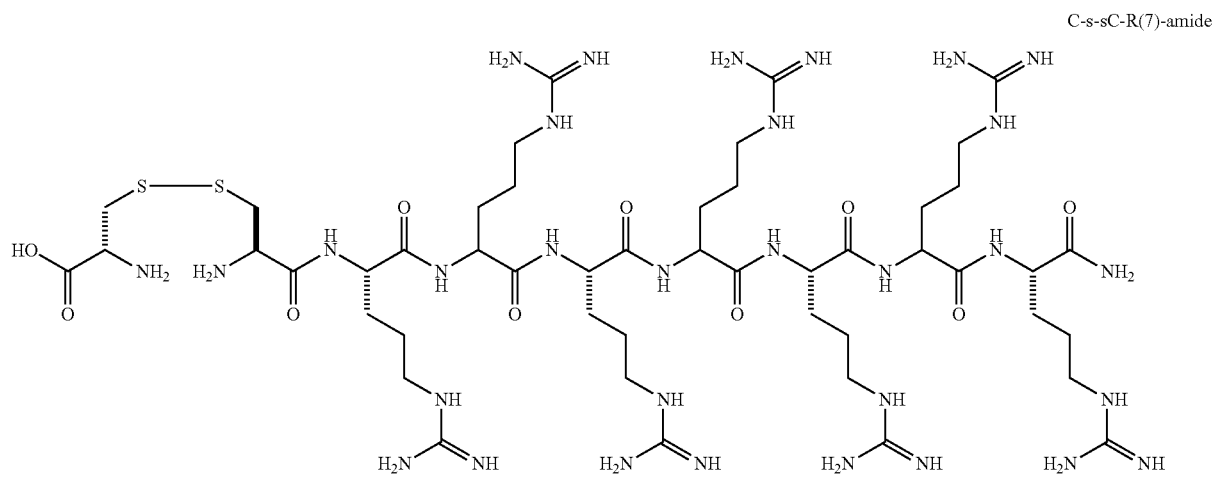

C-s-sC-R(7)-amide ("C-R(7)" disclosed as SEQ ID NO: 8)

By way of example, this composition might also be expressed as "C-s-s-C-R-R-R-R-R-R-R (SEQ ID NO: 8). This notation distinguishes the disulfide bond, present here, from a conventional peptide bond. The compositions depicted below are similarly expressed mutatis mutandis (SEQ ID NOS 9, 8, and 5, respectively, in order of appearance).

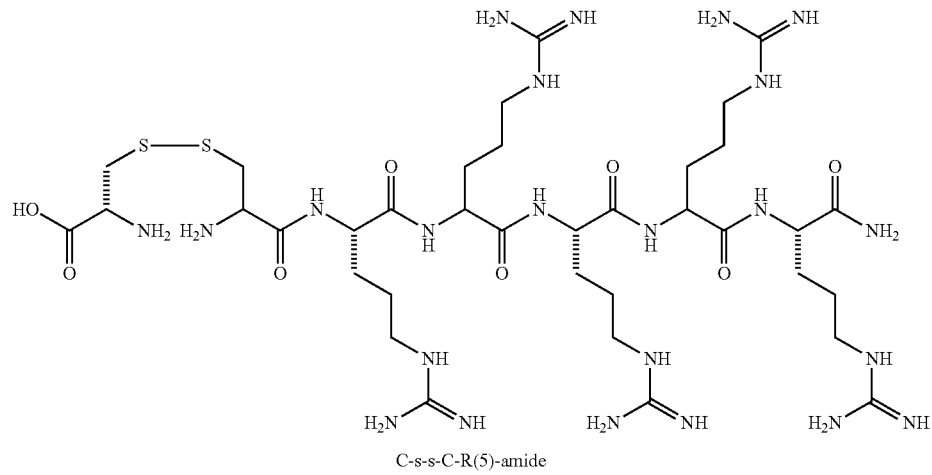

C-s-s-C-R(5)-amide

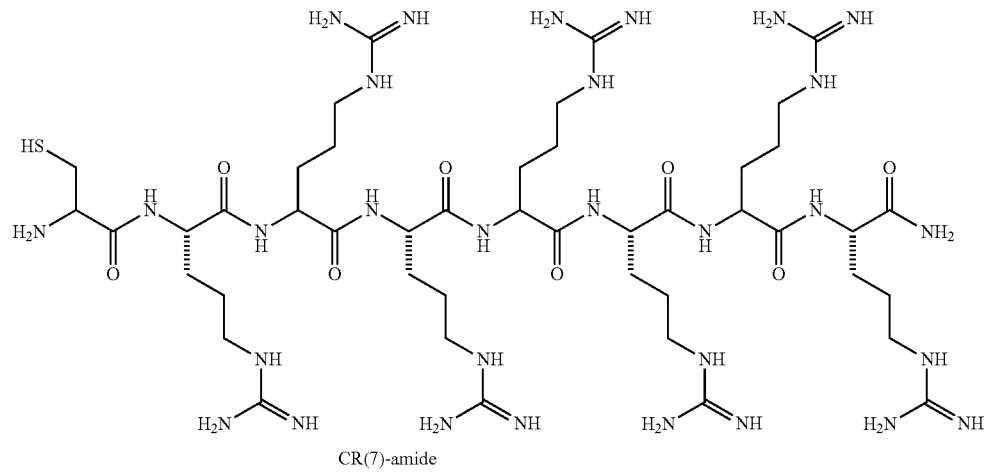

CR(7)-amide

-continued

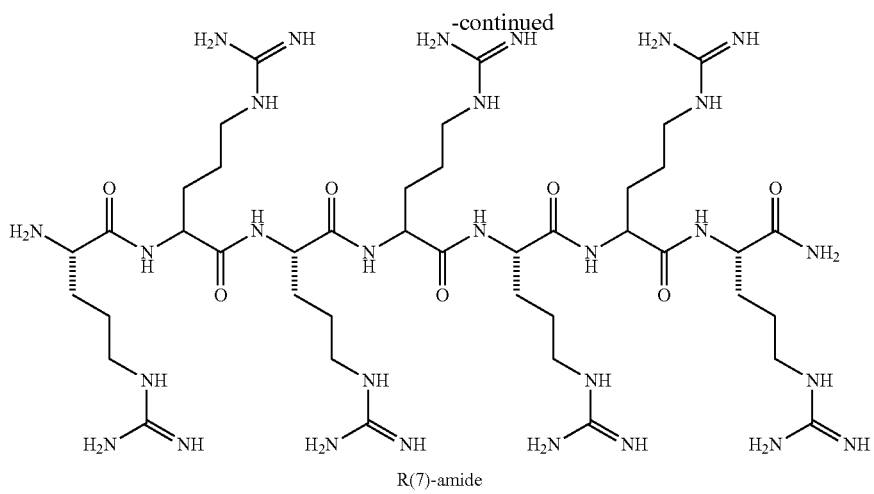

R(7)-amide

This invention includes a polyarginine peptide comprising from 5 to 9 arginines (SEQ ID NO: 1). In some embodiments this peptide further comprises 1 or more terminal cysteines. In some instances there are at least 2 terminal cysteines linked by a disulfide bond.

A particular polyarginine peptide of comprises C-s-s-CR-RRRRRR (SEQ ID NO: 8) where C is cysteine, C-s-s-C is a disulfide bond between 2 cysteines and R is arginine. Optionally this peptide the 2 cysteines are N-terminus linked.

In other embodiments the polyarginine peptide comprises CRRRRRRR (SEQ ID NO: 8), or comprises RRRRRRR (SEQ ID NO: 5).

The noted peptide may include at least 1 d-arginine and additionally at least 1 or more terminal cysteines which are d-cysteine.

Yet further embodiments of the polyarginine peptide comprise up to 2 terminal neutral amino acids.

This invention is further drawn to a therapeutic method of treating actual or anticipated neuronal injury comprising the step of administering a therapeutically effective dose of a polyarginine peptide of from 5 to 9 arginines (SEQ ID NO: 1). Optionally, the method further includes administering such peptide further comprising 1 or more terminal cysteines. In one embodiment the polyarginine peptide is C-s-s-CRRRRRRR (SEQ ID NO: 8). All methods of administration are contemplated including i.v. A useful range for methods of i.v. treatment dosing is from about 0.01 mg/kg to about 20 mg/kg.

This invention is yet further drawn to a method of protecting against glaucoma associated vision damage to at least one eye in a subject comprising administering to said subject a therapeutically effective dosage of the compositions described herein. Particular reference is made to a polyarginine peptide comprising from 5 to 9 arginines (SEQ ID NO: 1) and further comprising 1 or more terminal cysteines. Administration may be by any usual form including oral and by eye drops. Doses from about 0.1 to about 10 µg per 20 µl drop are noted.

DETAILED DESCRIPTION OF THE INVENTION

Without being bound by any particular theory, it is believed that the compositions of the present invention act to preserve mitochondria as function organelles, and that this influences the broadly observed neuroprotection disclosed herein.

Neuorprotection by C-R-R-R-R-R-R-R (SEQ ID NO: 8) (C is cysteine, R is arginine; composition termed "CR(7)" (SEQ ID NO: 8)) is effective when the peptide is made with either l- or d-amino acids. Dosing too is substantially l- or d-independent.

Without being bound by any particular theory, reference is made to the strong positive charge of the polyarginine compositions. E.g., over all charge of the peptide is +7 with 7 arginine residues (SEQ ID NO: 5). Notably, substituting lysine (also positively charged) for arginine in the presence or absence of a terminal cysteine did not provide neuroprotection.

Further, a peptide with at least 5 or more arginines (SEQ ID NO: 3) can be flanked by 1 or 2 neutral amino acids and still be therapeutically active. In such instances, cysteine, if present, is attached at the arginine end. By way of example, C-R-R-R-R-R-R-A (SEQ ID NO: 10), or, C-R-R-R-R-R-R-A-A (SEQ ID NO: 11), the A representing alanine which is neutral.

Dosing should be instituted is soon as possible after the subject presents with a neuronal injury; e.g., stroke-like indicia or Traumatic Brain Injury. Dosing is stated for R7 (i.e., 7 arginine peptide) (SEQ ID NO: 5) compositions, but is similar for all compositions disclosed herein. Broadly, therapeutically effective intraventricular dosages of from about 1,000 µg/kg to about 1 µg/kg are noted. For i.v administration, therapeutically effective dosages from about 20 mg/kg to about 0.01 mg/kg are noted. Oral, intrathecal, and indeed all forms of administration are contemplated.

For intravetricular injection particularly useful (but non-limiting) dosages ranges are R(7)-CC ("R(7)-C" disclosed as SEQ ID NO: 12):

high end: 500 µg/kg
low end: 5 µg/kg
R(7)-C (SEQ ID NO: 12)

high end: 450 µg/kg
low end: 4.5 µg/kg

-continued

R(7) (SEQ ID NO: 5)

High end: 400 µg/kg
Low end: 4.0 µg/kg

For dosing via i.v. injection in mg/kg/hr and assuming 20% remaining active following crossing of blood brain barrier.

R(7)-CC (N-terminus) ("C-R(7)" disclosed as SEQ ID NO: 8):

high end: 5 mg/kg
low end: 0.05 mg/kg
R(7)-C (N-terminus) (SEQ ID NO: 8)

high end: 4.5 mg/kg
low end: 0.045 mg/kg
R(7) (SEQ ID NO: 5)

High end: 4 mg/kg
Low end: 0.040 mg/kg

Dosing is contemplated to begin as soon as possible after the initial neuronal injury. Dosing may be daily for about 10, 20, or 30 days or more post-insult. Dosing every other day or varied regimens based in circulating blood levels of composition are contemplated.

I.v. infusion over the initial post-injury 1 to 10 hours is contemplated, but infusion may be usefully be administered daily for about 10, 20, or 30 days or more post-insult.
Composition Synthesis:

Disclosed arginine compositions can be prepared by a variety of well known synthetic techniques. In one embodiment standard fmoc-based protocols were used (Merrifield et al., J. Am Chem. Soc. (1963) 85, 2149-2155). The teachings of this and all references cited herein are incorporated by reference in their entirety.

Reference is made to the chiral nature of arginine and cysteine. Both l- and d-based compositions (e.g. d-R, d-C, l-R, l-C) were neuroprotective. The terminal cysteine(s) are contemplated as attached at either/both the N-terminus or C-terminus via peptide bond and to reduce the reactivity of the exposed SH group, will have the option of being protected by way of a disulfide linkage to a second cysteine (designated here as C-s-s-C).

In a test model, the retina was protected from NMDA-induced chemical stroke. Notably d-amino acid peptides are resistant to most protease digestion and, in some embodiments, exhibit longer half-life in vivo. The compositions of this invention are useful in a variety of clinical situations, most of which are characterized by neurological insult or cellular insult typified by mitochondrial damage. Without being bound by any particular theory, untreated mitochondrial damage is believed to lead to generation of free radical species. The compositions of this invention appear to avert or curtail oxidative stress in the retina following NMDA-insult by reducing mitochondrial originated free radical generation. Without being bound by any particular theory, such activity is believed to be significant in neuroprotection arising from the compositions of this invention.

Particular reference is made to neuronal injury such as stroke and Traumatic Brain Injury (including closed head injury, e.g. sports, accidental injury involving concussion, blast injury (combat or other). In one embodiment, football players and boxers are dosed prophylactically prior to a game, practice, or bout. Additionally dosing may be immediately after first contact in a scheduled game or bout. Dosing is based on an assumption of neurological insult or incipient damage without regard to actual (detected) presenting symptoms.

The pharmacologically active compositions of this invention can be processed in accordance with conventional methods of Galenic pharmacy to produce medicinal agents for administration to subjects, e.g., mammals including humans. The therapeutic compositions disclosed herein are usefully prepared an aqueous solutions. Particular not is made of isotonic saline. Other dosage forms are also contemplated. Particularly suitable are injectable, sterile solutions. Ampoules are convenient unit dosages.

It is also possible to freeze-dry the new compositions and use the lyophilisates obtained, for example, for the preparation of products for injection.

Dosages for a given host can be determined using conventional considerations, e.g., by customary comparison of the differential activities of the subject compositions and of a known agent, e.g., by means of an appropriate, conventional pharmacological protocol.

Attention is drawn to the uptake into brain tissues under in vivo conditions Fluorescent-tagged R(7) (SEQ ID NO: 5) and C-s-s-CR(7) ("CR(7)" disclosed as SEQ ID NO: 8) were injected into the vitreal chamber of a rat eyes and analyzed for specific uptake into retinal neurons at multiple time points post-injection. Both compounds demonstrated uptake into the retina within 30 min following injection and showed significant accumulations with retinal neurons and glia cells located in both the ganglion and inner nuclear layers of the retina. At longer time points (2-4 hrs post injection) the accumulation of the labeled peptides accumulated within the cytoplasm of the majority of neurons in the inner half of the retina with preferential accumulations being localized to small membrane-bound organelles surrounding the nucleus of both ganglion cells and amacrine cells as well as in exiting ganglion cell axons. Double labeling studies show that the majority of these labeled puncta colocalize with mitochondrial-specific markers, strongly implying that the R(7) (SEQ ID NO: 5) peptides are targeting the mitochondria.

Testing addressed intrathecal and intraventricular injection of fluorescent-tagged R(7) (SEQ ID NO: 5) and C-s-s-C-R(7) ("C-R(7)" disclosed as SEQ ID NO: 8). Both intrathecal and intraventricual injections of fluorescent-tagged CR(7) (SEQ ID NO: 8) show that the peptide readily crosses the pia matter glial barrier to accumulate in multiple populations of neurons in the spinal cord and in the brain. Preferential accumulation was noted in the neurons located within the hippocampus and cerebral cortex. This approach is a workable option for quick delivery to prevent both stroke or traumatic injury to these tissues.

Data establish that the compounds of the present invention protect the neural tissue (retina) against a strong NMDA-insult, with particular reference to R(7) (SEQ ID NO: 5), CR(7) (SEQ ID NO: 8) and C-s-s-CR(7) ("CR(7)" disclosed as SEQ ID NO: 8). Testing employed an in vivo rat retinal toxicity model that models neurochemically induced stroke (Goebel, D. J. and Winkler, B., J. Neurochem. 98:1732-1745, 2006). It has been documented that R(7) (SEQ ID NO: 5), CR(7) (SEQ ID NO: 8) and C-s-s-CR(7) ("CR(7)" disclosed as SEQ ID NO: 8) block short-term neuronal cell death signaling when administering a compound simultaneously with the induction of chemically induced stroke using the glutamate receptor agonist N-methyl-D-aspartate (NMDA). All three compounds listed above blocked NMDA-induced loss of plasma membrane selectivity in all NMDA-receptive neurons out to 8 hrs post-insult whereas retinas treated with NMDA-alone showed significant neuronal distress 2 to 4 hrs post insult. In addition, short-term (2-4 hrs post-NMDA-insult) biochemical studies also show that R(7) (SEQ ID NO: 5), CR(7) (SEQ ID NO: 8) and C-s-s-CR(7) ("CR(7)" disclosed as SEQ ID NO: 8) fully block NMDA-induced caspase activation, poly-(ADP)ribosylolation and mitochondrial-induced oxidative stress in the retina, all hallmarks for early signaling neuronal cell death in our system.

Both CR(7) (SEQ ID NO: 8) and C-s-s-CR(7) ("CR(7)" disclosed as SEQ ID NO: 8) demonstrated long-term protection against NMDA-induced retinal ganglion cell death 14-21 day post-insult, with both peptides providing protection that was not significantly different from results obtained from untreated or sham-treated control retinas. Although R(7) (SEQ ID NO: 5) provides full short-term protection. R(7) (SEQ ID NO: 5) was less effective in providing longer-term protection against retinal ganglion cell death using a single dosing. Repeated dosing is indicated to extend the period of protection.

Protection mediated by polyarginine requires a minimum of 5 consecutive arginine residues (SEQ ID NO: 3). Cysteine placement on either the amino- or carboxy-terminus of the poly-arginine peptide extends the neuroprotective action.

R(7)-C(SEQ ID NO: 12) treatment produced both short and long-term protection against an NMDA-insult that was shown not to be significantly different from retinas treated with CR(7) (SEQ ID NO: 8) or C-s-s-CR(7) ("CR(7)" disclosed as SEQ ID NO: 8).

Data compared peptides generated with d- and l-amino acid bases. Results also show that d-CdR(7) (SEQ ID NO: 13) and d-C-s-s-dCdR(7) ("dCdR(7)" disclosed as SEQ ID NO: 13) isomers provided full short- and long-term neuroprotection against and NMDA-insult and that the level of protection provided were not significantly different for the corresponding l-isoforms or untreated retina. These findings indicate that stereo-specificity of CR(7) (SEQ ID NO: 8) peptides is not required to mediate neuroprotection against an excitotoxic challenge.

Without being bound by ant particular, data indicate that R(7) (SEQ ID NO: 5), CR(7) (SEQ ID NO: 8) and C-s-s-CR(7) ("CR(7)" disclosed as SEQ ID NO: 8) block mitochondrial induced oxidative stress and attenuate mitochondrial hyperpolarization following excitotoxic stress. In one test, cultured HEK293 cells pretreated with R(7) (SEQ ID NO: 5), CR(7) (SEQ ID NO: 8) or C-s-s-CR(7) ("CR(7)" disclosed as SEQ ID NO: 8) were accessed for mitochondrial respiration changes in mitochondrial membrane potentials and for oxidative stress following a controlled chemically induced excitotoxic challenge to the cultured cells. Results showed that all three peptides showed significant attenuation in oxidative stress and in stress-induced hyperpolarization of the mitochondrial membrane potentials as compared with shame-treated controls. In addition, studies by our group also show that all three compounds significantly prevented mitochondrial oxidative stress, indicating that the peptides are either directly or indirectly targeting the mitochondrial to block them from initiating cell death signaling events linked to neuron cell loss Example 1

Stroke Patient

A 57 year old male enters the emergency room and is diagnosed with an ischemic event involving the middle cerebral artery, with symptomatology onset being under 1 hr. Immediately, the patient was administered an i.v. supplemented with poly-arginine (R(7)C-s-s-C ("R(7)C" disclosed as SEQ ID NO: 12), 5 mg/kg) while blood supply to the restricted area is restored. Daily testing of cognitive and motor systems show no deficits in physical or mental capacities. In addition, CT/MRI imaging show no signs of lesioning in the affected region, immediately following recovery and that this was maintained and confirmed by follow-up imaging and behavior testing.

Example 2

Post-Stroke Patient

A 64 year old woman is revived following stoke in her home by EMS and is rushed to the nearest hospital 80 miles away. Upon arriving at the hospital it is determined that the patient is showing signs of weakness on her left side. In addition she complains of having blurred vision and exhibits difficulty in speaking clearly. She is immediately started an i.v. and administered poly arginine (R(7) (SEQ ID NO: 5))@ 4 mg/kg/hr over a period of 5 days to arrest post-stroke neuronal damage. The patient is monitored for recovery signs. Improvement in her speech pattern is noted over the next 30 days as is increased muscle tone on the left side and muscle recovery strength and usage of her effected limbs.

Example 3

TBI Patient

A 17 year old high school football player is rushed to the emergency room of a local hospital suffering from a severe concussion following a helmet to helmet impact with an opposing player. The patient is initially unconscious on the field for over 20 min. EMS personnel arrived to find the patient responding to stimuli, but completely disoriented and unable to coordinate muscle movement, articulate speech or focus eye movements. Upon arriving at the ER, the patient is administered an i.v. containing R(7)C-s-s-C ("R(7)C" disclosed as SEQ ID NO: 12) peptide at 0.05 mg/kg. Delivery of the peptide continued until brain swelling resulting from the impact returns to normal state (3-5 days). Without being bound by any particular theory, the therapeutic is to arrest neuronal cell death resulting from these documented post-traumatic effects. Monitoring the patient though this period (and beyond) shows that he remains symptom free of TBI and post-concussion effects (i.e. avoiding short-term memory loss or exhibiting longer-term learning deficits.

Example 4

TBI Patient

The same scenario of Example 3 is noted except here, the polyarginine is R(7)-C (SEQ ID NO: 12) (C-Terminus) and the dosage is 4/mg/kg Example 5

TBI Patient

The same scenario of Example 3 is noted except here, the polyarginine composition is R(7) (SEQ ID NO: 5) and the dosage is 4 mg/kg.

Example 6

TBI Patient

The same scenario of Example 3 is noted except here, the polyarginine is R(7)C-C ("R(7)C" disclosed as SEQ ID NO: 12) and the dosage is 0.05 mg/kg.

Example 7

TBI Patient

The same scenario of Example 3 is noted except here, the polyarginine composition is R(7) (SEQ ID NO: 5) and the dosage is 0.04 mg/kg.

Example 8

Spinal Cord Injury

A 30 year old female presents with a spinal cord injury following an automobile accident. The subject is conscious but unable to move her legs. Multislice spiral computed tomography (MSCT) demonstrates a foreign body in spinal canal at the level of the Th11-Th12. A Th(11)-L(2) laminectomy is performed along with retrieval of foreign bodies and dura repair. Upon admission the patient is administered an i.v. containing R(7)C-s-s-C ("R(7)C" disclosed as SEQ ID NO: 12) peptide at 0.15 mg/kg. Delivery of the peptide is continued every other day for 30 days when substantial ability to move her legs is returned.

Example 9

Glaucoma Therapeutic

A 60 year old female presents with a complaint of blurry vision in her left eye for 1 week. Her IOP is above 21 mmHg. A diagnosis of glaucoma is made.

Effort is made to surgically reduce IOP. In post-surgical monitoring, IOP levels remain above normal excepted levels. To prevent retinal damage resulting from the prolonged exposure to elevated IOP. the patient is administered CR(7) (SEQ ID NO: 8) in the form of eye drops suspended in a corneal penetrating lipophilic suspension. Each 20 µl drop contains 1.25 µg of CR(7) (SEQ ID NO: 8) The total applied/treatment is 2.5 µg. Two drops are administered morning and two drops at night Treatment is continued chronically and no progression of neuronal cell death is detected.

The invention claimed is:

1. A therapeutic method of treating ischemic neuronal injury comprising administering a therapeutically effective dosage form of a polyarginine peptide consisting of from 5 to 9 arginines and 1 or more terminal cysteines.

2. The method of claim 1 wherein said polyarginine peptide is C-s-s-CRRRRRRR (SEQ ID NO: 8).

3. The method of claim 2 wherein administration is i.v.

4. The method of claim 3 wherein administration is from about 0.01 mg/kg to about 20 mg/kg.

5. The therapeutic method of claim 1 wherein said therapeutically effective dosage form of a polyarginine peptide consists of 9 arginines.

6. The therapeutic method of claim 1 wherein said therapeutically effective dosage form is oral dosage form or injectable solution.

* * * * *